(12) United States Patent
Hiemenz et al.

(10) Patent No.: US 10,596,312 B2
(45) Date of Patent: Mar. 24, 2020

(54) SYSTEM FOR IMPROVING FLUID DRAINAGE

(71) Applicants: Gregory John Hiemenz, Silver Spring, MD (US); Amit Navin Shah, North Potomac, MD (US)

(72) Inventors: Gregory John Hiemenz, Silver Spring, MD (US); Amit Navin Shah, North Potomac, MD (US)

(73) Assignee: InnoVital, LLC, Calverton, MD (US)

( * ) Notice: Subject to any disclaimer, the term of this patent is extended or adjusted under 35 U.S.C. 154(b) by 105 days.

(21) Appl. No.: 15/608,305

(22) Filed: May 30, 2017

(65) Prior Publication Data

US 2017/0348475 A1 Dec. 7, 2017

Related U.S. Application Data

(60) Provisional application No. 62/345,230, filed on Jun. 3, 2016.

(51) Int. Cl.
*A61M 1/00* (2006.01)
*A61M 3/02* (2006.01)

(52) U.S. Cl.
CPC ........ *A61M 3/0283* (2013.01); *A61M 1/0064* (2013.01); *A61M 3/022* (2014.02); *A61M 3/0241* (2013.01); *A61M 3/0262* (2013.01); *A61M 3/0287* (2013.01); *A61M 3/0295* (2013.01); *A61M 1/0013* (2013.01); *A61M 2205/3334* (2013.01); *A61M 2205/3344* (2013.01); *A61M 2205/36* (2013.01); *A61M 2205/583* (2013.01); *A61M 2210/101* (2013.01)

(58) Field of Classification Search
CPC ................ A61M 5/345; A61M 5/3134; A61M 5/31531; A61M 5/3129; A61M 5/3131; A61M 5/3132; A61M 5/3135
See application file for complete search history.

(56) References Cited

U.S. PATENT DOCUMENTS

| | | | | |
|---|---|---|---|---|
| 4,935,008 A | * | 6/1990 | Lewis, Jr. | ........... A61M 25/065 604/164.01 |
| 5,562,640 A | * | 10/1996 | McCabe | ............ A61B 17/0218 604/30 |
| 2007/0005002 A1 | * | 1/2007 | Millman | ............. A61M 1/0058 604/30 |

OTHER PUBLICATIONS

Ivey, K.M., White, C.E., Wallum, T.E., et al., 2012, "Thoracic Injuries in US Combat Casualties: A 10-Year Review of Operation Enduring Freedom and Iraqi Freedom," J Trauma Acute Care Surg, 73(6 Sup 5): S514-S519.

(Continued)

*Primary Examiner* — Rebecca E Eisenberg
(74) *Attorney, Agent, or Firm* — Royal W. Craig; Gordon Feinblatt LLC

(57) ABSTRACT

A low-cost and simple-to-use system and method to facilitate a prophylactic pleural lavage protocol at the time of thoracostomy tube placement for traumatic hemothorax in order to reduce the need for secondary intervention for the management of retained hemothorax. The invention may be used in conjunction with existing chest tubes and be administered at the time of initial chest tube placement, and continued at the bedside (by a bedside nurse) over the duration of chest drainage, as necessary. The system includes an operator device that semi-automatically administers a pleural lavage protocol consisting of saline instillation, and suction to slow the clotting process, prevent "gelling" of blood, and maintain drainability.

28 Claims, 4 Drawing Sheets

(56) References Cited

OTHER PUBLICATIONS

Mowery, et al., "Hemothorax and Occult Pneumothorax, Management of," J. Trauma, Feb. 2011, vol. 70, No. 2, pp. 510-518.
Mowery et al, supra; see also, Wim G. Boersma, Jos A. Stigt, Hans J. M. Smit., Treatment of Haemothorax, Respir Med. Nov. 2010, 104(11): 1583-1587.
Kimbrell BJ, Yamzon J, Petrone P, Asensio JA, Velmahos GC, Intrapleural Thrombolysis for the Managementof Undrained Traumatic Hemothorax: A Prospective Observational Study., J Trauma 62(5):1175-9 (2007).
Rezende Neto JB, Patore Neto M, Hirano ES, Rizoli S, Nascimento Jr B, Fraga GP, Management of Retained Hemothoraces After Chest Tube Thoracostomy for Trauma. Rev Col Bras Cir. 39(4) (2012); Chou, Lin, and Wu, "Video Assisted Thoracoscopic Surgery for Retained Hemothorax in Blunt Chest Trauma," Current Opinion in Pulmonary Medicine, vol. 21, 2015, pp. 393-398.
Tomaselli F, Maier A, Renner H, Smolle-Juttner FM, Thoracoscopical Water Jet Lavage in Coagulated Hemothorax, Eur J Cardiothorac Surg. 23(3):424-5 (2003).
Boyacioglu, et al., "A New Use of Fogarty Catheter: Chest Tube Clearance," Heart, Lung and Circulation, vol. 23, pp. e229-e230 (2004); Shiose, et al., "Improved Drainage with Active Chest Tube Clearance," Interactive Cardiovascular Thoracic Surgery, vol. 10, No. 5, pp. 685-688 (2010).
Kugler, N.W., Carver, T.W., and Paul, J.S., "Prophylactive Pleural Lavage Decreases Secondary Intervention in Patients with Traumatic Hemothorax," ASCA 39.09; Kugler NW, Carver TW, Milia DJ, Paul JS, "Thoracic Irrigation Prevents Retained Hemothorax: A Prospective Propensity Score Matched Analysis," Presented at Western Trauma Association. Mar. 6, 2016.

\* cited by examiner

SYSTEM FOR IMPROVING FLUID DRAINAGE

CROSS-REFERENCE TO RELATED APPLICATIONS

The present application derives priority from U.S. Provisional Patent Application 62/345,230 filed 3 Jun. 2016.

BACKGROUND OF THE INVENTION

1. Field of the Invention

The present invention relates to drainage devices for surgical procedures and, more particularly, to a system for improving drainage from a cavity within a human or animal body that breaks up clots or reduces clotting and/or thickening of the fluid to facilitate drainage.

2. Description of the Background

Trauma is the leading cause of death for US civilians under age forty with an incidence of 140,000 deaths per year. Thoracic injuries occur in approximately 60% of polytrauma cases and are a primary or contributing factor in up to 75% of all civilian trauma-related deaths. Ivey, K. M., White, C. E., Wallum, T. E., et al., 2012, "Thoracic Injuries in US Combat Casualties: A 10-Year Review Of Operation Enduring Freedom And Iraqi Freedom," J Trauma Acute Care Surg, 73(6 Sup 5): S514-S519; Mowery, et al., "Hemothorax and Occult Pneumothorax, Management of," J. Trauma, February 2011, Vol. 70, No. 2, pp. 510-518. Hemothorax, an accumulation of blood in the pleural space, is a common result of chest trauma. In the U.S. alone, the incidence of trauma-related hemothorax approaches 300,000 cases per year. Mowery et al, supra; see also, Wim G. Boersma, Jos A. Stigt, Hans J. M. Smit., Treatment of Haemothorax, Respir Med. 2010 November, 104(11): 1583-1587.

The primary treatment of hemothorax is tube thoracostomy. Thoracostomy typically involves placement of a large bore (36Fr to 42Fr) catheter (thoracostomy tube or chest tube) for drainage of the pleural space. Mowery et al, supra. Due to the likelihood of a combined pneumothorax, chest tubes for thoracic trauma are typically placed superiorly, as notionally illustrated in FIG. 1. While the majority of traumatic hemothoraces are managed by tube thoracostomy alone, in 3-30% of cases a measurable amount of blood remains in the chest after chest tube placement, a condition known as retained hemothorax, as notionally illustrated in FIG. 2. Kimbrell B J, Yamzon J, Petrone P, Asensio J A, Velmahos G C, Intrapleural Thrombolysis For The Managementof Undrained Traumatic Hemothorax: A Prospective Observational Study., J Trauma 62(5):1175-9 (2007); Rezende Neto J B, Patore Neto M, Hirano E S, Rizoli S, Nascimento Jr B, Fraga G P, Management Of Retained Hemothoraces After Chest Tube Thoracostomy For Trauma. Rev Col Bras Cir. 39(4) (2012); Chou, Lin, and Wu, "Video Assisted Thoracoscopic Surgery for Retained Hemothorax in Blunt Chest Trauma," Current Opinion in Pulmonary Medicine, Vol. 21, 2015, pp. 393-398.

There are several reasons why a hemothorax may not completely drain—ranging from the sheer volume of blood, the clotting process proceeding more rapidly than the draining process, and patient positioning relative to tube position (i.e., the tube is not in the dependent position). Retained hemothorax (RH) is typically diagnosed via computed tomography (CT) with chest CT imaging often triggered by a finding of persistent x-ray opacity after tube thoracostomy. Empyema, a bacterial or frankly purulent collection in the pleural space, results in 33% percent of RH cases that are visible on x-ray even after chest tube placement (typical RH volume >500 mL). Patients with RH are 12-16 times more likely to develop post-traumatic empyema than those chest trauma patients who do not develop RH. Brims et al., "Empyema Thracis: New Insights Into An Old Disease" European Respiratory Review, Vol. 19, No. 117, pp. 220-228. As such, RH is an independent risk factor for empyema, a condition with a 15-20% mortality rate (higher in immunocomprised patients). RH is also associated with subsequent adverse outcomes such as fibrothorax and trapped lung. While the maximum size of an RH that may be managed without secondary intervention has been debated, correlations between RH size and complications such as empyema and trapped lung have driven current recommendations to administer a secondary therapy (typically surgery) for RH's larger than 500 mL or ⅓ of the hemithorax. Mowery, et al., supra, Boersma et al, supra.

While studies investigating administration of an intrapleural thrombolytic for RH have shown limited success, current recommendations call for early video assisted thoracoscopic surgery (VATS). 39(4). Chou et al, supra. In VATS, a thoracoscope and surgical instruments are inserted into the chest cavity via 1-3 relatively small incisions. The ipsilateral lung is collapsed to obtain a clearer view of the pleural cavity. Adhesions are then released via blunt digital dissection or sharp endoscopic electrocoagulated dissection and blood and clots are removed by standard suction or a suction-irrigator system. Sponge sticks and ring forceps can enable careful removal of organized collections and some studies have investigated the use of jet-lavage to more efficiently remove adherent clots and membranes without damaging the pleura. Early VATS has been shown to decrease the incidence of empyema and pneumonia and rapidly restore lung function. Chou et al, supra. Compared to previous surgical approaches to RH (i.e. thoracotomy), VATS has been reported to have fewer postoperative complications, less pain, fewer wound and pulmonary complications, shorter recovery time, and shorter length of hospital stay. As a result, VATS has become a preferred primary management option for RH—even over the placement of a second chest tube.

VATS intervention, however, is not without costs and contraindications. Most notably VATS requires a high level of expertise and resources—a skilled thoracic surgeon, an anesthesiologist to perform special intubation and lung drop, as well as significant support staff and equipment. Moreover, the careful removal of coagula adhering to underlying structures with limited visibility usually proves very time consuming and tiresome, and thus, costly work. Tomaselli F, Maier A, Renner H, Smolle-Juttner F M, Thoracoscopical Water Jet Lavage In Coagulated Hemothorax, Eur J Cardiothorac Surg. 23(3):424-5 (2003). In fact, these requirements for specialized equipment and personnel, as well as their associated costs, have been noted as barriers to widespread use of VATS. Milanchi, S., Makey, I., McKenna, R., & Margulies, D. R., "Video-Assisted Thoracoscopic Surgery in the Management of Penetrating And Blunt Thoracic Trauma, Journal of Minimal Access Surgery, 5(3), 63-66. Because it requires single-lung anesthesia, VATS is not only costly and time consuming, but also contraindicated for hemodynamic instability. VATS is also contraindicated for patients with spinal injuries and pulmonary disease or otherwise compromised lung function. Milanchi et al, supra.

It would be preferable to avoid the need for surgical intervention by actively preventing an RH and improving the drainage performance of conventional tube thoracostomy. While attempts at actively clearing the chest tube via Fogarty balloon catheters and other active clearance products have shown some reduction in the amount of retained blood, these devices do little to improve drainage of fluid beyond the distal tip of the chest tube. Boyacioglu, et al., "A New Use of Fogarty Catheter: Chest Tube Clearance," Heart, Lung and Circulation, Vol. 23, pp. e229-230 (2004); Shiose, et al., "Improved Drainage with Active Chest Tube Clearance," Interactive Cardiovascular Thoracic Surgery, Vol. 10, No. 5, pp 685-688 (2010).

Additionally, the use of a sterile suction catheter to evacuate the pleural space prior to chest tube insertion has shown modest reduction in duration of tube drainage and need for secondary intervention. Interestingly, a limited recent study demonstrated a lower rate of secondary intervention after prophylactic pleural lavage using warm saline at the time of thoracostomy tube placement and suctioning via a suction catheter advanced into the thoracostomy tube. Kugler, N. W., Carver, T. W., and Paul, J. S., "Prophylactive Pleural Lavage Decreases Secondary Intervention in Patients with Traumatic Hemothorax," ASCA 39.09; Kugler N W, Carver T W, Milia D J, Paul J S, "Thoracic Irrigation Prevents Retained Hemothorax: A Prospective Propensity Score Matched Analysis," Presented at Western Trauma Association. Mar. 6, 2016.

Despite an array of successful clinical results most trauma surgeons do not regularly perform thoracic lavage due to real or perceived difficulty and time intensity of the manual procedure, insterility of the procedure, or other reasons. What is needed is a flexible, low-cost and easy-to-use system that enables rapid pleural lavage via the existing chest tube in a completely sterile manner.

SUMMARY OF THE INVENTION

It is, therefore, a primary object of the present invention to provide a system and method for pleural lavage, both at the time of thoracostomy tube placement and subsequent to tube placement, for traumatic hemothorax in order to reduce the need for secondary intervention for the management of retained hemothorax.

It is another object to provide a system and method as above that is simple and efficient to use, employing familiar tubing connections and control valves, and which deploys a rapid, automated saline infusion process, thereby minimizing training requirements and barriers to adoption.

It is another object to provide a system and method to facilitate a prophylactic pleural lavage as above that enables easy transition from lavage, to high wall suction, to low pressure chest drain suction without breaking the sterile circuit.

It is still another object to provide a system and method that allows adjustment of the lavage protocol (e.g., amount of infused saline per lavage cycle, number of lavage cycles at time of tube placement), and repetition of lavage at a later time based upon clinical indications.

It is still another object to provide a system and method that allows other future therapies/procedures to be administered through the chest tube without breaking the sterile circuit, such as introduction of a fibrinolytic solution, the use of a balloon catheter for tube clearance and/or pneumatic agitation at the distal tip of the chest tube, etc.

In accordance with the foregoing objects, the invention disclosed herein is a low-cost and simple-to-use system and method to facilitate a prophylactic pleural lavage protocol at the time of thoracostomy tube placement for traumatic hemothorax in order to reduce the need for secondary intervention for the management of retained hemothorax. The invention may be used in conjunction with existing chest tubes and be administered at the time of initial chest tube placement, and continued at the bedside (by a bedside nurse) over the duration of chest drainage, as necessary. The system includes a lavage controller that semi-automatically administers a pleural lavage protocol consisting of instillation of warmed saline into the pleural space and suction to slow the clotting process, prevent "gelling" of blood, and maintain drainability.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENT

The present invention is a system to facilitate a prophylactic rapid pleural lavage protocol at the time of thoracostomy tube placement for traumatic hemothorax in order to reduce the need for secondary intervention for the management of retained hemothorax.

Figure 2:
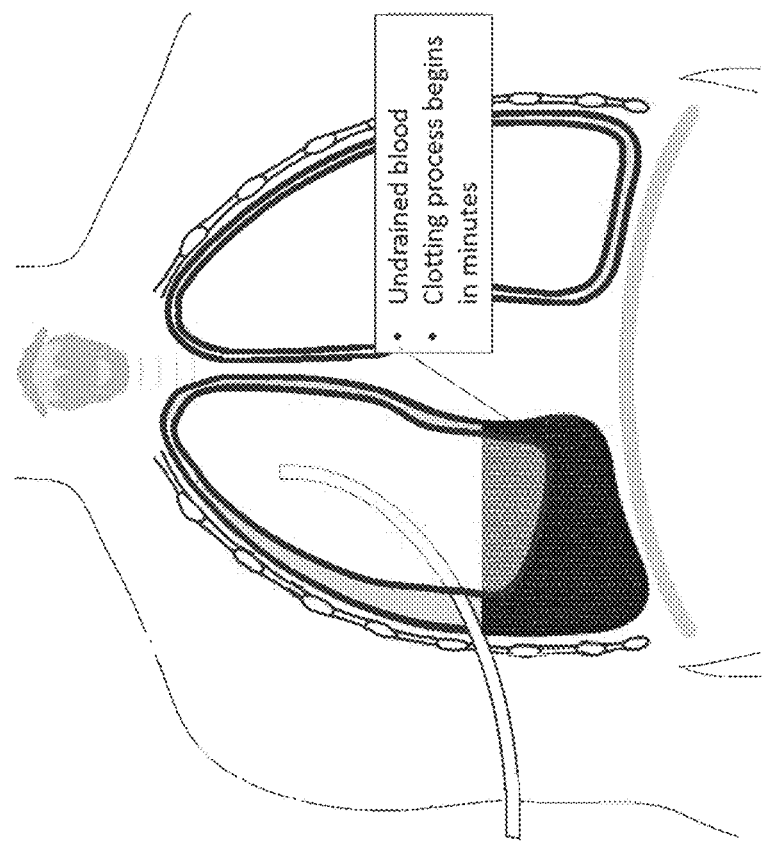
FIG. 2 is a perspective diagram illustrating how undrained blood tends to remain in the lower and posterior pleural space.
Figure 1:
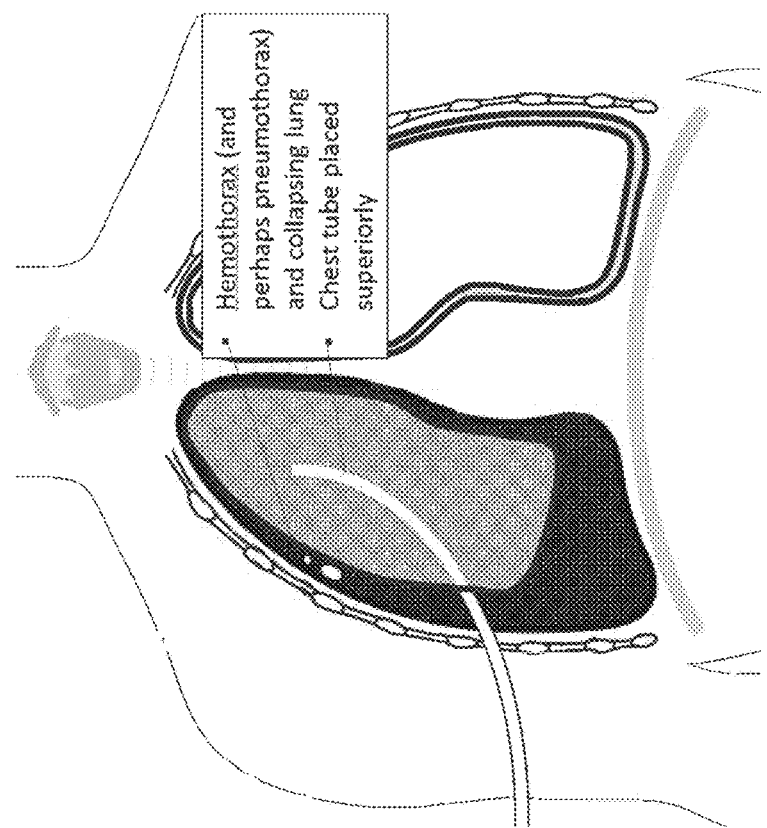
FIG. 1 is a perspective diagram illustrating a chest tube initially placed superiorly.
Figure 3:
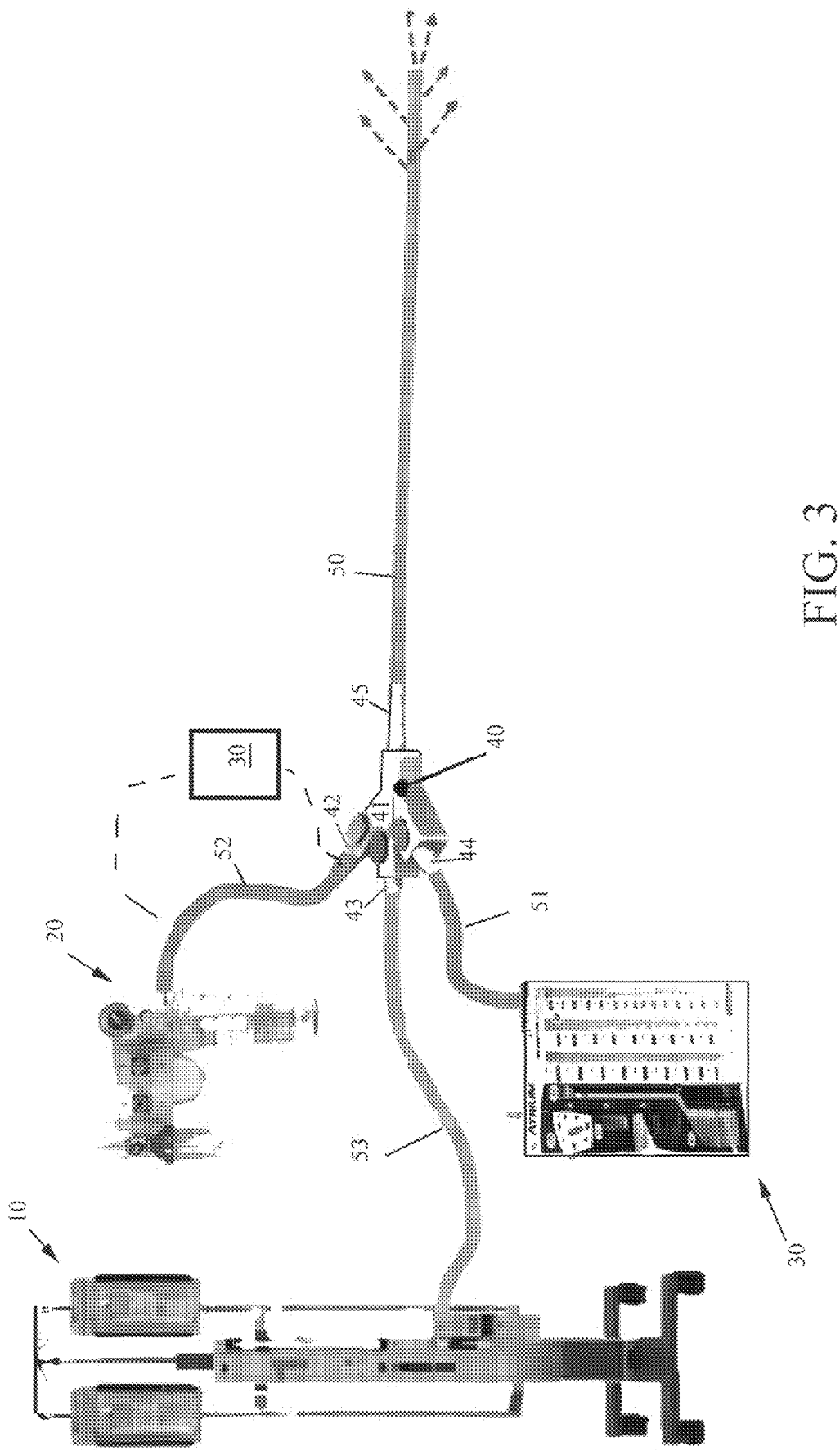
FIG. 3 is a perspective drawing showing how the system of the present invention connects to standard hospital equipment to enable switching between pressurized lavage, high pressure suction, and standard low pressure chest drain.

As seen in FIG. 3, the present system includes a rapid saline infuser 10 configured for infusion of saline into the pleural cavity. Preferably the saline infuser 10 and thoracostomy tube should be configured for emptying a 1000 cc saline bag in at most 30 seconds, and optimally should be configured for emptying a 1000 cc the same bag in 20 seconds, the latter enabling a 500 cc lavage in 10 seconds. It is also preferable for the saline infuser to warm the saline to substantially average body temperature prior to infusion. In the illustrated embodiment, the saline infuser 10 comprises a commercially available rapid infuser by Level 1™, Inc., which includes a fast flow rate fluid warmer capable of sustained flow rates in a range of from 30 ml/min to 1100 ml/min with a maximal rate of 1400 ml/min through a small bore peripheral venous catheter (typically 20 gauge needle with 0.6 mm internal diameter). These flow rate specifications depend on Poiseuille's law, the variables being the internal diameter (D) and length (L) of the chest tube, the viscosity of the liquid (h) and the pressure of the saline infuser 10. If the diameter of a tube is doubled, flow will increase by a factor of 16, implying that small increases in the size of drainage tubes will result in large increases in flow rates. Traditionally, large bore (>28 F, 9 mm internal diameter) catheters are recommended in almost all situations that required chest drainage. Given the substantial difference in internal diameter between a peripheral venous catheter and traditional thoracostomy tube, the rapid infuser will be capable of providing significantly higher flow rates through a thoracostomy tube. Similar commercial products are available from Belmont™ or Thermacor™. Alternatively, a manual pressure infusion bag may be used such as the Infu-Surg® pressure infusion bag. Manual pressure infusion bags are very low cost and ubiquitous at hospitals, and operate in the same manner and at the same pressures (~300 mmHg) as the above-described rapid infusers. However, they lack the automation for warming and pressurizing the saline. Nevertheless, tests conducted by the present inventors demonstrated that, when pressurized to 300 mmHg, a manual pressure infusion bag was likewise capable of emptying a 1000 cc the same bag in 20 seconds. Still another option for the saline infuser is to use a suction/irrigation pump such as the StrykeFlow™ II system manufactured by Stryker, or a Stryker AHTO system. The StrykeFlow II is a battery-operated, fully disposable fixed-flow-rate pump that hangs from the saline bag and operates by generating negative pressure within the tubing to draw fluid from the IV bag. The Stryker AHTO, on the other hand, features a reusable pump, with three flow rate settings up to 4 L/min. However, the goal here is to impart a 500 mL lavage in just a few seconds and current surgical irrigation pumps are less-well suited for this. Finally, saline infuser 10 may also function via more passive/manual means such as gravity or ambient air pressure. For example, the saline infuser 10 may consist of simply a saline bag that is hung at a height above the patient such that it passively flows into the patient's pleural space. Similarly, the saline infuser 10 may simply be a funnel into which saline is poured. In addition to the saline infusion device 10, a conventional low pressure chest drain 30 is provided along with a conventional high-pressure suction unit 20. Typical chest drainage systems connect to a suction source and include a pressure regulator, seal, and collection chamber. The seal typically consists of a water seal or dry seal (one way valve) that allows air to exit from the pleural space on exhalation, while preventing air from entering the pleural cavity or mediastinum on inhalation. For present purposes the chest drainage system 30 may be a three-chamber drainage system such as the Pleur-evac™ available from Teleflex, Inc., and suction unit 20 may be a conventional surgical suction pump may be used such as a Medala™ Basic.

Three ports to a pleural lavage controller 40 are connected in fluid communication with the chest drainage system 30, suction unit 20, and rapid saline infuser 10 via tubes 51, 52, 53, respectively. If desired, an optional second collection chamber or chest drainage system 30 may be connected inline between suction unit 20 and port 42 to drain the contents of tube 52, as shown in dotted lines in FIG. 3. The ports of lavage controller 40 are manifolded to a single port that is connected to a standard chest tube 50 for administering a protocol consisting of saline instillation, chest drainage, and suction to slow the clotting process, prevent "gelling" of blood, and maintain drainability over the duration of chest drainage. Importantly, the lavage controller 40 facilitates easy transition from lavage via the rapid saline infuser 10, to high wall suction via the suction unit 20, to low pressure chest drain via the unit 30 all without breaking a sterile circuit. Moreover, using the lavage controller 40 a clinician can tailor the lavage protocol (e.g., amount of infused saline per lavage cycle, and number of lavage cycles at time of tube placement) and repeat the lavage at a later time based upon clinical indications. In addition, the lavage controller 40 provides flexibility for other future therapies/procedures to be administered through the chest tube 50 without breaking the sterile circuit, such as introduction of a fibrinolytic solution, and/or the use of a balloon catheter for tube clearance and/or pneumatic agitation at the distal tip of the chest tube 50, etc.

The present system may be easily assembled at the time of chest tube 50 placement to preserve sterility. For example, if the balloon catheter (FIG. 4) is to be used, there are two options:

1) simply disconnect tube 53 from lavage controller 40 and introduce the balloon catheter via the same port 43 (this is convenient but may slightly compromise sterility of the circuit);

2) provide a balloon catheter that is preconnected off of a Y in tube 53, but housed in a plastic sleeve until use. That is, when advancing the balloon catheter through the chest tube 50, the plastic sleeve scrunches up. Then when withdrawn from the chest tube 50 the balloon catheter remains housed in the plastic sleeve. This approach will prevent the user from ever breaking the sterile circuit.

Figure 4:
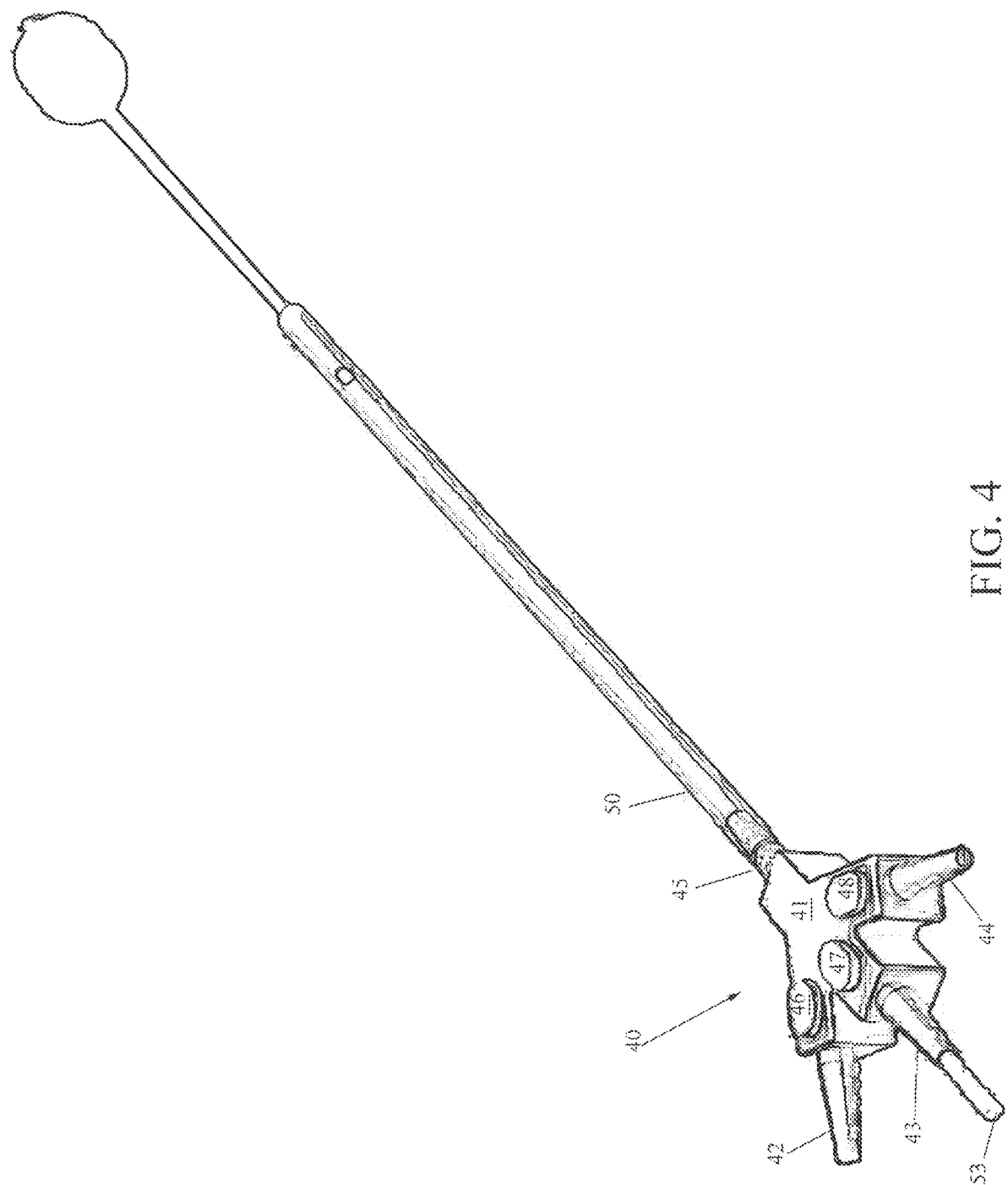
FIG. 4 is a perspective view of a balloon catheter being advanced through the chest tube via the lavage controller of the system of FIG. 3.

FIG. 4 is a close-up view of the lavage controller 40 with three input ports 42, 43, 44 manifolded to a single port 45 that is connected to standard chest tube 50. FIG. 4 also depicts a balloon catheter 53 that has been inflated after introduction through the chest tube 50 via port 43 and through port 45. The lavage controller 40 generally comprises a molded housing 41 with three ports 42, 43, 44 manifolded to a single port 45 that is connected to standard chest tube 50.

Each of the four ports 42-45 comprises a frustoconically-shaped outward protrusion that tapers outwardly from the housing 41, and defined by a central lumen and annular-exterior ribs or steps. The frustoconical shape enables connection to variously-sized tubes 50-53 and the annular ribs/steps prevent dislodgement of the tubes 50-53 once inserted thereon.

Figure 5:
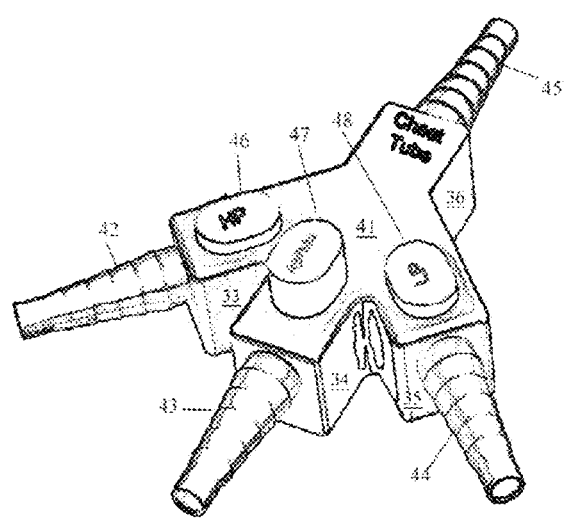
FIG. 5 is an isometric view of the lavage controller of FIG. 4 showing a spring-return locking detent valve.

As seen in FIG. 5, the housing 41 is shaped as a three-pronged trident with three distinct branching chambers each axially aligned with one port 42-44, all converging to an axis, and one coaxial trailing chamber for the port 45. The port 45 extends directly rearward and is axially aligned with and in fluid communication with the chamber. The three ports 42-44 are aligned with and in fluid communication with the chambers. Importantly, the three ports 42-44 and their respective chambers axially converge at shallow angles not exceeding 45 degrees to ensure "soft" fluid branching there through, effectively reducing the risk of clogging by minimizing torturous fluid pathways. Each chamber of the housing 41 is equipped with a spring-return locking detent valve 46, 47, 48 for stopping or allowing fluid flow from each port 42-44 to port 45. In some embodiments of the invention, any of spring-return locking detent valves 46, 47, 48 may be a finger-valve. The spring-return locking detent valves 46, 47, 48 are marked with proper indicia for designating the port (HP for high pressure, LP for low pressure, and Ag/Tube for saline infusion), both to indicate which port 42-44 is being actuated and which tube to connect. Similarly, the port 45 is marked with proper indicia to indicate connection of the chest tube 50.

Figure 6:
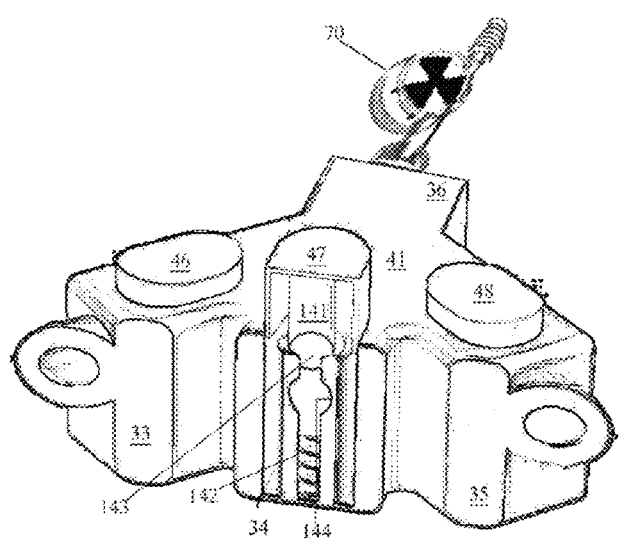
FIG. 6 is a perspective illustration of controller 40 with a cutaway view of an exemplary spring-return locking detent valve.

FIG. 6 is a perspective illustration of controller 40 with a cutaway view of an exemplary spring-return locking detent valve 47. Detent valve 47 comprises an oval open-bottom button with a closed top and vertical sidewalls. The sidewalls slide vertically into a conforming channel formed in housing 41. A vertical post 141 protrudes downward from the top of the button into a tubular receptacle formed in housing 41, which serves to selectively allow/stop fluid flow. A spring 142 underlies the post 141 and biases it to a normally-closed upward position shown. However, the post 141 has an aperture 143 traversing it, which aperture aligns with a conduit 144 through the housing 41 when the button and post 141 are depressed to allow fluid flow.

The illustrated detent valves 46-48 are preferably all biased by spring 142 to their normally-closed position. This generally prevents high pressure suction or lavage ports from inadvertent locking in an open position. However, it may be desirable to lock the valve 48 to low pressure chest drain 30 (See FIG. 3) in an open position, Any suitable locking arrangement may be used for this. For example, the valve 48 button may include an extensional flap or strap to engage a cooperating feature on the controller body 41. Alternatively a more complicated push-to-lock mechanism may be used similar to those in retractable pens. A variety of such mechanical locking means are disclosed such as by U.S. Pat. No. 8,157,242. Conversely, it may be desirable to lock all ports in a closed position to prevent someone from inadvertently introducing therapy. Again, any suitable locking arrangement may be used for this. For example, as shown in FIG. 6 while in their normally-closed (up) position the spring-return locking detent valves 46, 47, 48 may be twisted so that it no longer fits back inside the conforming channel formed in housing 41. Optionally, it may be desirable to prevent someone from opening more than one detent valve 46, 47, 48 at any time. A mutually exclusive locking arrangement can be accomplished with a suitable protrusion from each valve button that will interfere with a cooperating protrusion on another button if depressed. For the standard low pressure drain valve, we would want this to be lockable in the open position.

In addition to the foregoing, an integral flow meter, visual flow indicator or pressure gauge 70 may be included such as shown in FIG. 6 to provide immediate visualization of flow. Flow indicator 70 may be a conventional visual flow indicator such as a Bel-Art Roto-Flo™. Flow indicator 70 may be coupled at any port. For example, flow meter can be placed in line with the rapid saline infuser 10 (See FIG. 3) via tube 53 (See FIG. 4) to measure flow rate (rate of rotation) or even total volume (number of turns) instilled. The flow meter/indicator may be linked optionally to controller 40 (See FIG. 4) to provide an electrical or mechanical auto-stop feature after it rotates a predetermined number of times. Moreover, a pressure gauge may be optionally linked to controller 40 to provide a similar auto-stop feature.

Each of the spring-return locking detent valves 46, 47, 48 provide instantaneous control over the respective fluid flow to facilitate a prophylactic pleural lavage that enables easy transition from lavage, to high wall suction, to low pressure chest drain suction without breaking the sterile circuit. Moreover, the controller 40 (See FIG. 4) is simple and efficient to use, employing familiar tubing connections and control valves, and establishes a rapid, automated saline infusion process, thereby minimizing training requirements and barriers to adoption. The system as a whole can be deployed at the time of thoracostomy tube placement for traumatic hemothorax to reduce the need for secondary intervention for the management of retained hemothorax.

Having now set forth the preferred embodiments and certain modifications of the concepts underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

We claim:

1. A pleural lavage controller, comprising:
    a housing comprising a plurality of fluid chambers, including a first fluid chamber and a second fluid chamber both in fluid communication with a third fluid chamber;
    a plurality of fluid ports each in fluid communication with one of said plurality of chambers, including a first port in fluid communication with said first fluid chamber, a second port in fluid communication with said second fluid chamber, and a third port in fluid communication with said third fluid chamber;
    a chest tube connected to said third fluid port;
    said third fluid port having a frustoconically-shaped outward protrusion that generally tapers inwardly away from said housing and bears a plurality of exterior raised grips comprising a first grip having a first maximum circumference and a second grip having a second maximum circumference that is less than the first maximum circumference, and spaced along said outward protrusion for releasably connecting said third fluid port to a plurality of indwelling catheters, at least two of said plurality of indwelling catheters having different connection tube circumferences; and
    a plurality of finger-valves comprising a finger-valve in each of said first fluid chamber and second fluid chamber for selectively admitting and preventing fluid flow-through from the corresponding fluid port to said third fluid port connected to said indwelling catheter.

2. The pleural lavage controller of claim 1 further comprising a fourth fluid chamber that is in fluid communication with said third fluid chamber; said fourth fluid chamber being in fluid communication with a fourth port.

3. The pleural lavage controller according to claim 1, wherein each of said ports is frustoconical.

4. The pleural lavage controller according to claim 1, wherein said housing comprises distinct outward protrusion corresponding to each of said first fluid port, second fluid port and third fluid port.

5. The pleural lavage controller according to claim 1, wherein said plurality of finger valves each comprise a detent valve configured to be depressed into said corresponding fluid chamber for affecting fluid flow through said fluid chamber.

6. The pleural lavage controller according to claim 5, wherein each said detent valve comprises a locking mechanism configured to lock the detent valve in a depressed position in said corresponding fluid chamber.

7. The pleural lavage controller according to claim 6, wherein each said detent valve comprises a spring-return locking mechanism.

8. The pleural lavage controller according to claim 5, wherein each said detent valve comprises an open-bottom button with a closed top and sidewalls, and a post protruding downward from the top of the button.

9. The pleural lavage controller according to claim 8, wherein said housing comprises an annular slot for receiving the sidewalls of said detent valve and a central tubular receptacle for receiving said post.

10. The pleural lavage controller according to claim 9, further comprising a spring in said receptacle for biasing said post.

11. The pleural lavage controller according to claim 8, wherein said post and said receptacle both have transverse apertures configured to selectively align by depression of said detent valve causing axial depression of said post into said central tubular receptacle.

12. The pleural lavage controller according to claim 1, further comprising a flowmeter mechanically coupled to at least one of said plurality of finger-valves.

13. The pleural lavage controller according to claim 1, further comprising a pressure gauge mechanically coupled to at least one of said plurality of finger-valves.

14. The pleural lavage controller according to claim 1, further comprising a suction source in fluid communication with one of said first or second fluid ports.

15. The pleural lavage controller according to claim 14, further comprising a seal connected between said pleural lavage controller and said suction source.

16. The pleural lavage controller according to claim 14, wherein said plurality of fluid ports further comprises a fourth fluid port in fluid communication with said suction source, said fourth fluid port being manifolded with said second fluid port and said third fluid port to said first fluid port.

17. The pleural lavage controller according to claim 14, further comprising a drainage collection chamber connected between one of said first or second fluid port and said suction source.

18. The pleural lavage controller according to claim 1, further comprising a fluid infuser connected to one of said first or second fluid ports.

19. The pleural lavage controller according to claim 18, wherein said fluid infuser comprises a fluid warmer.

20. The pleural lavage controller according to claim 18, wherein said fluid infuser is configured for emptying a 1000 cc fluid container in 30 seconds or less.

21. The pleural lavage controller according to claim 20, wherein said fluid infuser comprises a saline fluid infuser configured for emptying a 1000 cc fluid container in 20 seconds or less.

22. The pleural lavage controller according to claim 21, wherein said saline infuser comprises an electromechanical pressure infuser.

23. The pleural lavage controller according to claim 21, wherein said saline fluid infuser comprises a pump for applying negative pressure on a fluid.

24. The pleural lavage controller according to claim 18, wherein said fluid infuser applies external positive pressure to a fluid.

25. The pleural lavage controller according to claim 24, wherein said external positive pressure is applied by one of gravitational acceleration or ambient air pressure.

26. The pleural lavage controller according to claim 24, wherein said external positive pressure is applied manually.

27. The pleural lavage controller according to claim 1, wherein said housing is shaped with three distinct branching chambers including said first fluid chamber axially aligned with said first fluid port, said second fluid chamber axially aligned with said second fluid port, and said third fluid chamber axially aligned with said third fluid chamber.

28. The pleural lavage controller according to claim 1, wherein said first chamber and said second chamber branch to said third chamber at angles not in excess of 45 degrees.

* * * * *